United States Patent [19]
Buratto

[11] Patent Number: 5,935,140
[45] Date of Patent: Aug. 10, 1999

[54] METHOD FOR MODIFYING THE CURVATURE OF THE CORNEA

[76] Inventor: Lucio Buratto, Piazza Della Repubblica No. 21, Milan, Italy

[21] Appl. No.: 08/904,151

[22] Filed: Jul. 31, 1997

[51] Int. Cl.$^6$ ..................................................... A61F 9/00
[52] U.S. Cl. ............................................................ 606/166
[58] Field of Search ................................... 606/166, 167, 606/174, 1, 5; 604/4–6, 10–18, 1

[56] References Cited

U.S. PATENT DOCUMENTS

| | | | |
|---|---|---|---|
| 3,818,913 | 6/1974 | Wallach | 128/305 |
| 4,180,075 | 12/1979 | Marinoff | 128/305 |
| 4,298,004 | 11/1981 | Schachar et al. | 128/305 |
| 4,676,790 | 6/1987 | Kern | 623/5 |
| 4,840,175 | 6/1989 | Feyman . | |
| 5,288,292 | 2/1994 | Giraud et al. | 606/166 |
| 5,533,997 | 7/1996 | Ruiz | 606/5 |
| 5,549,622 | 8/1996 | Ingram | 606/166 |
| 5,556,406 | 9/1996 | Gordon et al. | 606/166 |
| 5,658,303 | 8/1997 | Koepnick | 606/166 |

OTHER PUBLICATIONS

L. Burrato, et al., "Excimer Laser Intrastromal Keratomileusis: Case Reports," *Journal of Cataract Refract. Surg,* vol. 18, Jan. 1992, pp. 37–41.
L. Burrato, et al., "Excimer Laser Intrastromal Keratomileusis," *Journal of Opthalmology,* vol. 113, No. 3, Mar. 15, 1992, pp. 291–295.
L. Burrato, et al., "Indications, Techniques, Results, Limits, and Complications of Laser in situ Keratomileusis," *Current Opinions in Opthalmol.,* Rapid Science Publishers, 1997, 8:IV, pp. 59–66.
L. Burrato, et al., "Myopic Keratomileusis With the Excimer Laser: One–Year Follow Up," *Refractive & Corneal Surgery,* vol. 9. Jan./Feb. 1993, pp. 12–19.
L. Burrato, "Down–up LASIK is Latest Chapter in Development of Lamellar Refractive Surgery," *Ocular Surgery News International,* Thorofare: Slack Inc. 1996; 7(11), pp. 22–23.

*Primary Examiner*—Michael Buiz
*Assistant Examiner*—Vy Q. Bui
*Attorney, Agent, or Firm*—Smith, Gambrell & Russell, LLP; Beveridge, DeGrandi, Weilacher & Young Intellectual Property Group

[57] ABSTRACT

This invention is for a surgical method for modifying the curvature of the cornea. The method involves making a semicircular lamellar cut on the cornea to form a superficial layer which remains connected to the cornea in a superior zone so as to form a flap. The superficial is raised to expose the underlying surfaces which are subjected to the desired ablation. The superficial layer is then replaced over the underlying surface so as to adhere. By forming a flap with the connecting hinge region in a superior zone, the flap which is raised during the operation and then replaced will be smoothed over the remaining part of the cornea under the effects of the blinking movement of the eyelid and by gravity. This encourages the distension and centering of the superficial layer and enhances the effects of the ablative treatment. The method of the invention also provides greater ease and convenience to the surgeon performing the method.

15 Claims, 1 Drawing Sheet

METHOD FOR MODIFYING THE CURVATURE OF THE CORNEA

FIELD AND BACKGROUND OF THE INVENTION

1. Field of the Invention

This invention relates to a method for modifying the curvature of the cornea with particular application in the correction of myopia.

2. Background of the Invention

Over the last few years myopic keratomileusis has been subjected to rapid and significant technical and surgical evolution to such a degree that it is now the elective technique for the correction of moderate-severe ametropias and the main subject of debate in international congresses which deal with keratorefractive surgery. It appears that with slight ametropias, the reliability and the stability of the results offered by the technique of Photo Refractive Keratectomy (PRK (the modification of the corneal surface using excimer lasers)) is reasonably satisfactory. However, it also appears that current PRK techniques are not in a position to provide adequate predictability and long-term stability for the correction of more severe refractive defects. These objectives are reached more satisfactorily if the refractive procedure is performed on the intrastromal site; this will also avoid direct damage to the Bowman's membrane, a complication which is responsible for the well-known post-ablative haze and the expected long-term regression of the results.

The refractive procedure, when performed directly on the stroma will save the Bowman's membrane, reduce tissue reactivity, lower the dependency on corticosteroid treatment and more importantly, obtain a refractive result that is both predictable and stable over time. For these reasons, the international scientific interest is largely directed towards intrastromal keratomileusis particularly following the development of excimer lasers and the techniques for photoablation of the stroma. The most recent approach towards keratomileusis is the so-called LASIK technique.

The LASIK technique involves the use of a keratotome, an electromechanical and pneumatic device which performs circular corneal resections to create flaps with more or less parallel faces and pre-determined diameter and thickness. The keratotome or microkeratome, depending on the specific model, may also be automated. The instrument is also fitted with a stop mechanism to block the run of the blade (or other cutting device) and prevent a full circle (360°) corneal disk from being cut. This allows the surgeon to perform a cut which stops 1–1.5 mm from the end of the run and thus creates a hinge. This technique allows the surgeon to lift the flap which has been cut, place it on the nasal side, and expose the underlying stromal bed to the refractive in situ procedure using the excimer laser. The flap is then replaced and remains in position also under the influence of the uncut portion (the hinge). This technique allows the surgeon to perform a lamellar cut on the front surface of the cornea involving the superficial layer of the cornea. This cut extends in a circular direction but stops before the completion of 360° so that the superficial layer (flap) remains attached to the remaining part of the cornea in the nasal zone by means of this hinge.

The superficial layer (flap) is then raised and moved to one side to expose the surfaces underlying the cornea; these are subjected to in situ ablation using the excimer laser and the curvature of the cornea is modified to the desired value. Finally the superficial layer (flap) which was previously moved to the nasal side is returned to the surface, which have now been ablated, and it (the flap) adheres to the stromal bed without sutures being used.

There have been some problems with this technique which have come to light during the course of the trials. The superficial layer which remains attached to the underlying cornea in the nasal sector during the operation (the hinge which remains attached and has not been cut) cannot prevent the movement of the superficial layer during the vertical blinking movements of the eyelid. The superficial layer remains attached to the underlying tissue more for the effect of the endothelial pump rather than for purely mechanical reasons. So the superficial layer with the nasal hinge can move and the movement is one of the most frequent complications observed in the post-operative period during the learning curve of this procedure. The complication will arise particularly if the flap is re-positioned incorrectly at the end of the operation, if the superficial layer does not adhere sufficiently to the underlying stromal bed in the immediate post-operative and more generally if there are defects in the epithelium or excessive lachrymation.

Moreover with this technique, it can happen that the superficial layer is positioned incorrectly. It can be replaced in a position which is slightly decentered upwards, downwards or nasally. It may also happen that it has not been smoothed sufficiently which will result in the formation of intralamellar folds which will persist post-operatively and interfere with the visual function. In the best scenario, the blinking action of the eyelids will not interfere with the flap but in the worst scenario it can actually increase the degree of dislocation and/or the number of folds.

Another problem inherent to this operating technique is the fact that the superficial layer which has been cut, has been placed nasally for the time necessary to perform the refractive procedure with the laser. In the event of small-diameter lamellar cuts or ablations on large optical zones there is the risk that the stromal surface of the flap will also accidentally be ablated (the part that has been exposed by raising the flap and turning it over). In order to avoid this possibility, the hinge should be protected.

In actual practice, the nasal hinge limits the extension of the ablation in the nasal sector which may reflect on the final refractive outcome and more specifically the visual function (the area not treated nasally). This is particularly important in the case of with-the-rule astigmatism because the ablation is done along the horizontal axis and the treatment involves wide-ablation zones. Laser ablation involves the removal of tissue. The central depth of the ablation is proportional to the degree of myopia, the optic zone chosen and whether or not multi-zone treatments are being used. If, for example, the surgeon performs a treatment for 10 myopic diopters on a single 5.5 mm zone, the depth of the ablation at the center will be about 100 microns. So therefore, between the center of the ablation and the zone which has not been treated, there will be a difference in depth of about 100 microns.

The intrastromal 'vacuum' left by the laser ablation is filled by the lamella or the superficial layer which adapts to the underlying bed. However, there are a number of problems. The formation of lamellar microfolds which are more numerous and obvious when the ablation is deeper and there is no transition zone, can, post-operatively, negatively affect the visual performance. In the classical operating technique LASIK, under the influence of the nasal hinge, the lamella can not be positioned uniformly around the 360°. This involves nasally—oriented micromovements of the lamella and influences the arrangement of the folds which will extend nasally.

SUMMARY OF THE INVENTION

The objective of this invention is to resolve some of the above-mentioned problems by developing a technique which will modify the curvature of the cornea and provide for better adhesion of the raised layer at the end of the operation and the correct re-positioning of the flap on the remaining part of the cornea. Within the scope of this objective is to obtain a superficial area of the cornea (flap) which is raised during the operation and, when replaced, will be smoothed over the remaining part of the cornea under the effects of the blinking movement of the eyelid.

This method of this invention also encourages the smoothing and distention and the centering of superficial layers of the cornea (corneal flap) raised during the operation, even though the flap will sometimes tend to be decentered slightly temporally or nasally.

Further features and advantages of the method described in this paper can be seen in the Detailed Description of the Invention.

DETAILED DESCRIPTION OF THE INVENTION

Figure 1:
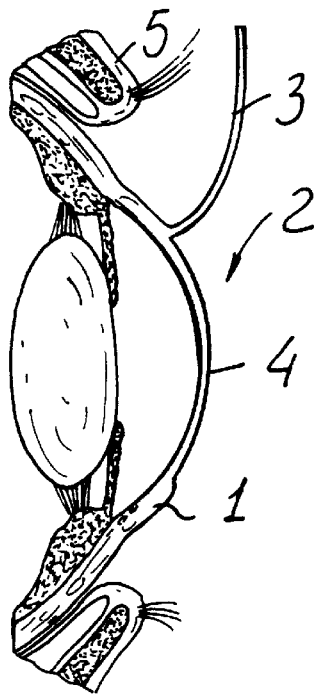
FIG. 1 is a cross-sectional view of the eye with the corneal flap lifted.
Figure 2:
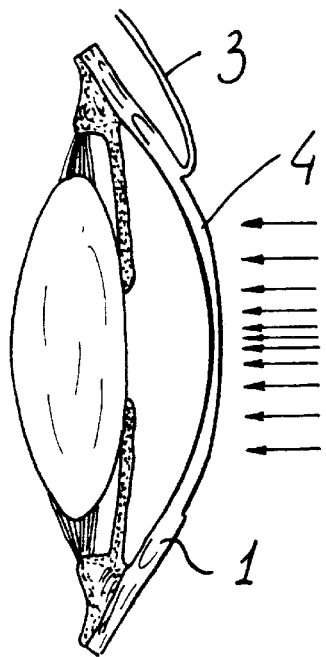
FIG. 2 is a cross-sectional view of the eye showing the areas of the cornea which have been modified.
Figure 3:
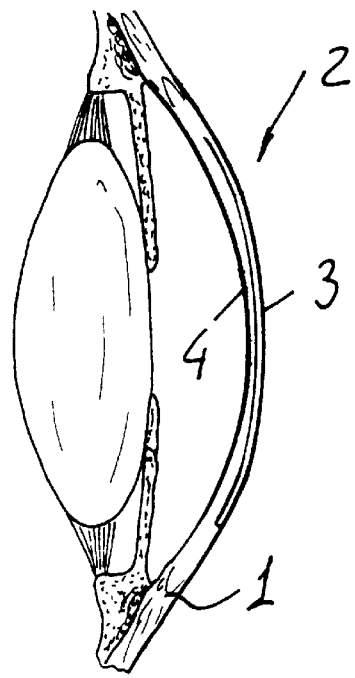
FIG. 3 is a cross-sectional view of the eye showing repositioning of the corneal flap.

The present invention is a surgical cutting technique which allows the surgeon to modify the curvature of the cornea particularly for the surgical correction of refractive ametropias, and consists of the following phases:

- a lamellar cut performed on the anterior surface of the cornea involving one superficial layer of the cornea; the cut extends for an incomplete circle to keep this superficial layer attached to the remaining part of the cornea in a superior zone.
- raising of the superficial layer to expose the underlying surfaces of the cornea
- completion of an in situ ablation on the above-mentioned underlying surfaces to modify the curvature of the cornea to the desired value
- repositioning of the superficial layer to the underlying surfaces which were subjected to ablation, without sutures being used.

Drawings 1–3 illustrate the sequence of this technique.

With reference to the numbers in the above-mentioned drawings, the method described in this paper is basically a lamellar cut performed on the frontal (anterior) surface of the cornea (1) of the eye (2) involving its superficial layer (3). The cut extends for an incomplete circle to maintain the superficial layer (3) connected to the remaining part of the cornea (1) in a superior zone with a hinge-type connection. In practice, the superficial layer (3) is connected to the remaining part of the cornea in the superior zone only as opposed to the nasal zone as in the classical well-known LASIK technique.

The lamellar cut is performed as usual with the microkeratome or alternately the surgeon can use any other device which can create circular corneal resections with predominantly parallel sides of predetermined diameter and thickness. The flap is usually about 9 mm in diameter for a thickness of 160 microns and extends around the superficial layer is raised, taking advantage of the connection to the remaining part of the cornea (1) to expose the underlying surfaces (4) of the cornea. These surfaces are then subjected to in situ ablation to modify the curvature of the cornea to the desired value. The operation of in situ ablation is performed using a laser or other method to remove a layer of tissue within well-defined parameters. Ideally the ablation is deeper in the center and more superficial in the peripheral areas and encompasses an area at least 6 mm in diameter. This is specific for myopic correction.

In defects such as hyperopia, astigmatism and presbyopia, the amount and position of tissue removed depends on the type of defect and should give the cornea the correct optical curvature.

Finally, the superficial layer (3) is repositioned on the underlying surface (4) which was subjected to ablation, in order obtain adequate natural adhesion of the flap which does not require sutures (sutureless technique). The operation has now been completed.

Compared to the classical Lasik technique i.e. the technique with a nasal hinge, the new technique with the superior hinge described in this paper, provides better adhesion of the superficial layer (3) to the underlying surface of the cornea. In fact the upper eyelid (5) exerts a continuous movement from the top downwards which helps maintain the superficial layer (3) in its position and facilitates its distention. Moreover, the force of gravity itself will tend to push the superficial layer (3) into an optimal position for adhesion.

The down-up movement of the upper eyelid associated with the compression it exerts encourages the distention and centering of the superficial layer (3) even if it is moderately decentered temporally or nasally.

With this new technique the astigmatic treatment is greatly enhanced by the absence of the nasal hinge. The astigmatic ablation (and more so the spherical ablation) can also be performed with a wider optical zone. With astigmatism in particular (but also in the other ametropias) the new technique allows the surgeon to use all available laser software; this is particularly true for lasers which use scanner treatments. If there are any limits to the ablation, with this technique they will remain in the corneal area which remains covered by the upper eyelid (5). The compression-distention effect exerted by the upper eyelid (5) tends to restrict the formation of microfolds deriving from the intrastromal vacuum left by the laser ablation even when the ablation of the underlying cornea is particularly deep.

In the classical Lasik technique, the epithelial microlesions can induce 'foreign body' sensations along the cutting line during blinking; this will cause weeping with the superficial layer tending to float in the lachrymal fluid or it will give the patient the sensation of a foreign body thereby causing the patient to rub their eye. Both these situations can act to displace the superficial layer. With the new method, there is a reduced possibility of this superior epithelial damage.

It should be noted that the functioning of instruments fitted with the eye tracker can be disturbed by the presence of devices placed nasally to protect the superficial layer which has been folded laterally. As a result, the patient and the surgeon will miss out on the advantages of this important precision device. With the present invention, however, the instrument which protects the cornea is in the superior zone and so does not interfere greatly (if at all) with the normal functioning of the eye-tracker.

In the event of post-operative enhancement, with the classical Lasik technique the procedure involves lifting the superficial layer of the temporal side to place it nasally; this will expose the underlying layers to the in situ treatment to correct the residual defect.

So as the epithelial defect is also found in the upper quadrant, the patient will often have a foreign body sensation, particularly when the eyelid moves during blinking. Moreover, the distention of the superficial layer after the enhancement may not be optimal.

With the present invention, the replacement is simpler and healing is more rapid. The induced irritation from the foreign body sensation is also reduced because the superior portion of the cornea is intact.

It should be pointed out that the method of the invention can be performed using a microkeratome, surgical blades, surgical lasers, or other cutting instruments (jets of water, liquid or other fluid, gas etc.). Moreover, with the method of the invention, the surgeon will be in a more comfortable position (assuming that the surgeon himself is performing the cut). These benefits provide for a more comfortable technique for both patient and surgeon than is obtained with the classical Lasik method.

Modifications and applications of the invention will be obvious to those skilled in the art and are intended to be encompassed by the disclosure of the present invention.

While a specific embodiment of the invention has been show and described in detail to illustrate the application of the principles of the invention, it will be understood that the invention may be embodied otherwise without departing from such principles and that various modifications, alternate constructions, and equivalents will occur to those skilled in the art given the benefit of this disclosure. thus, the invention is not limited to the specific embodiment described herein, but is defined by the appended claims.

I claim:

1. A method for modifying the curvature of the cornea for the correction of ametropias comprising;

performing a lamellar cut on the surface of a cornea extending for an incomplete circle so as to form a superficial layer connecting to the cornea in a superior zone;

raising the superficial layer to expose an underlying surface of the cornea;

performing an ablation or removal of tissue on the underlying surface to modify a curvature of the cornea; and replacing the superficial layer onto the underlying surface.

2. A method as in claim 1 wherein the lamellar cut is performed using a microkeratome.

3. A method as in claim 1 wherein the lamellar cut is performed using a surgical blade.

4. A method as in claim 1 wherein the lamellar cut is performed using a surgical laser.

5. A method as in claim 1 wherein lamellar cut is performed by water or other fluid/liquid/gas-based cutting instruments.

6. A method as in claim 1 wherein the lamellar cut has a diameter of about 9 mm with a thickness of about 160 microns and a circumferential extension of about 300° around a pupillary axis.

7. A method as in claim 1 where the ablation or removal of tissue is performed with an instrument selected from the group consisting of an excimer laser, a surgical laser, a water cutting device, a fluid cutting device, a liquid cutting device, and a gas cutting device.

8. A method as in claim 1 to correct myopia wherein the ablation is performed on a zone of the underlying surface and wherein the zone is deeper in the center and more superficial in the peripheral areas.

9. A method as in claim 1 to correct hyperopia wherein the ablation is performed on a zone of the underlying surface and wherein the zone is deeper in the peripheral areas and more superficial in the central areas.

10. A method as in claim 1 to correct astigmatism wherein the ablation is performed on a zone of the underlying surface and wherein the zone is deeper on a first meridian and more superficial along a second meridian.

11. A method as in claim 1 to correct presbyopia wherein the ablation is performed on a zone of the underlying surface and wherein the zone is ablated eccentrically.

12. A method as in claim 1, wherein the superficial layer has a stromal surface and wherein prior replacing the superficial layer onto the underlying surface, the stromal surface of the superficial layer is dehydrated in order to encourage adhesion of the superficial layer to the underlying surface.

13. A method as in claim 1, wherein the superficial layer has a stromal surface and wherein the superficial layer is glued onto the underlying surface with a biological glue.

14. A method as in claim 1, wherein the superficial layer has a stromal surface and wherein prior replacing the superficial layer onto the underlying surface, the stromal surface of the superficial layer is bathed with a viscous adhesive liquid to encourage adhesion of the superficial layer to the underlying surface.

15. A method as in claim 1, wherein the superficial layer has a stromal surface and wherein prior replacing-the superficial layer onto the underlying surface, the stromal surface of the superficial layer is sutured to the underlying surface to encourage adhesion of the superficial layer to the underlying surface.

* * * * *